(12) United States Patent
Ma et al.

(10) Patent No.: US 8,452,374 B2
(45) Date of Patent: May 28, 2013

(54) APPARATUS AND METHOD FOR SUBSTANTIALLY IMMOBILIZING A BREAST FOR MEDICAL IMAGING PROCEDURE

(75) Inventors: Kayan Ma, Toronto (CA); Gal Sela, Toronto (CA); Cameron Piron, Toronto (CA)

(73) Assignee: Hologic, Inc., Marlborough, MA (US)

( * ) Notice: Subject to any disclaimer, the term of this patent is extended or adjusted under 35 U.S.C. 154(b) by 306 days.

(21) Appl. No.: 12/851,988

(22) Filed: Aug. 6, 2010

(65) Prior Publication Data

US 2011/0034796 A1 Feb. 10, 2011

Related U.S. Application Data

(60) Provisional application No. 61/272,009, filed on Aug. 6, 2009.

(51) Int. Cl.
*A61B 5/055* (2006.01)
*H05G 1/00* (2006.01)

(52) U.S. Cl.
USPC .......................................... 600/415; 378/208

(58) Field of Classification Search
USPC .................. 600/407, 411, 415, 426; 378/37, 378/208; 128/845
See application file for complete search history.

(56) References Cited

U.S. PATENT DOCUMENTS

| 6,229,145 | B1 | 5/2001 | Weinberg |
| 7,656,993 | B2 * | 2/2010 | Hoernig ............................ 378/37 |
| 7,970,452 | B2 * | 6/2011 | Piron et al. ..................... 600/411 |
| 8,050,736 | B2 * | 11/2011 | Piron et al. ..................... 600/415 |
| 2007/0092059 | A1 | 4/2007 | Eberhard et al. |
| 2008/0230074 | A1 | 9/2008 | Zheng et al. |

FOREIGN PATENT DOCUMENTS

| WO | 9608199 A1 | 3/1996 |
| WO | 2008064271 A2 | 5/2008 |
| WO | 2010078048 A2 | 7/2010 |
| WO | 2011014966 A1 | 2/2011 |

OTHER PUBLICATIONS

International Search Report for International Application No. PCT/CA2010/001228 mailed Oct. 2, 2011, 5 pages.

* cited by examiner

*Primary Examiner* — Michael Rozanski
(74) *Attorney, Agent, or Firm* — Lando & Anastasi, LLP

(57) ABSTRACT

Apparatus and methods are described for substantially immobilizing a breast for use in medical imaging. In an exemplary embodiment, an apparatus for substantially immobilizing a breast is provided, including a first support member connected to a first and second base, the bases capable of engagement with the torso of a patient, the first support member defining an inner area substantially covered by a first membrane. A corresponding second support member, defining a second inner area substantially covered by a second membrane, is engageable to the first support member such that the inner areas are substantially aligned to substantially immobilize a breast, the membranes defining a pocket to receive a breast.

25 Claims, 18 Drawing Sheets

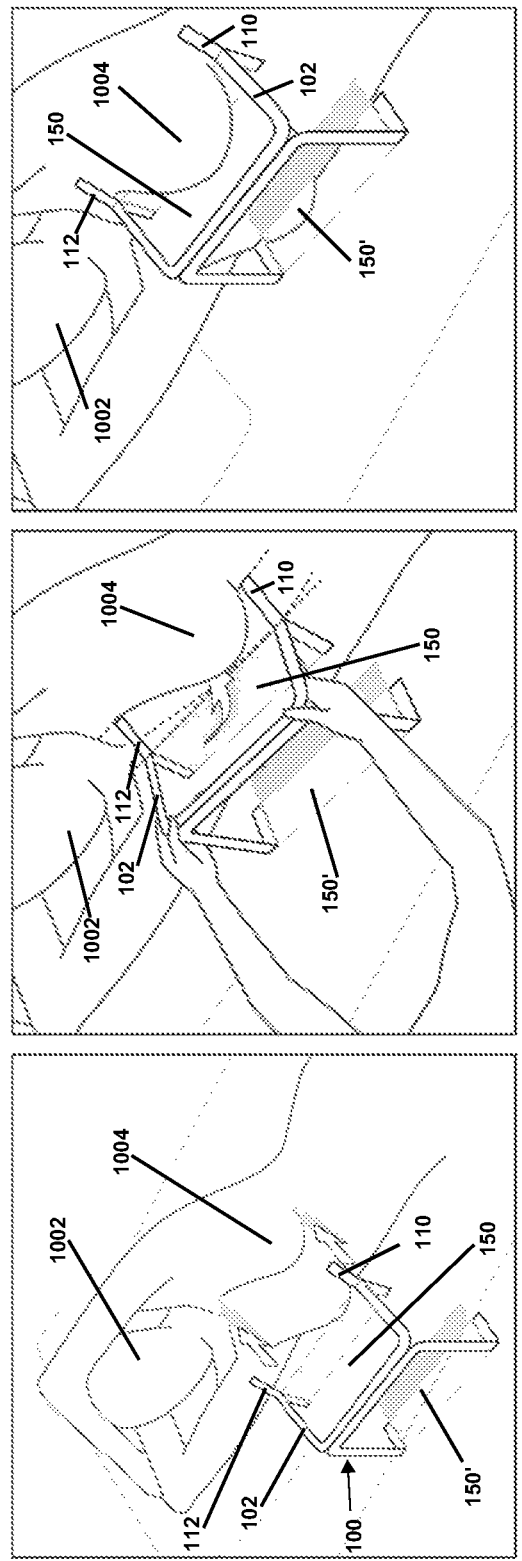

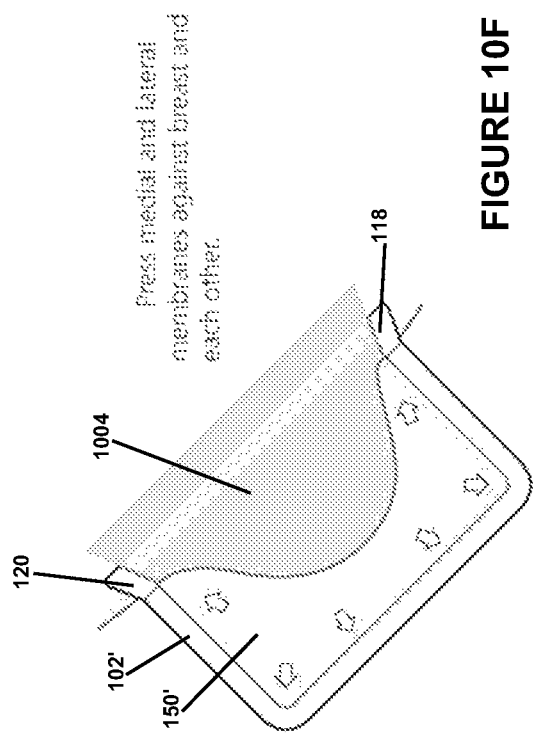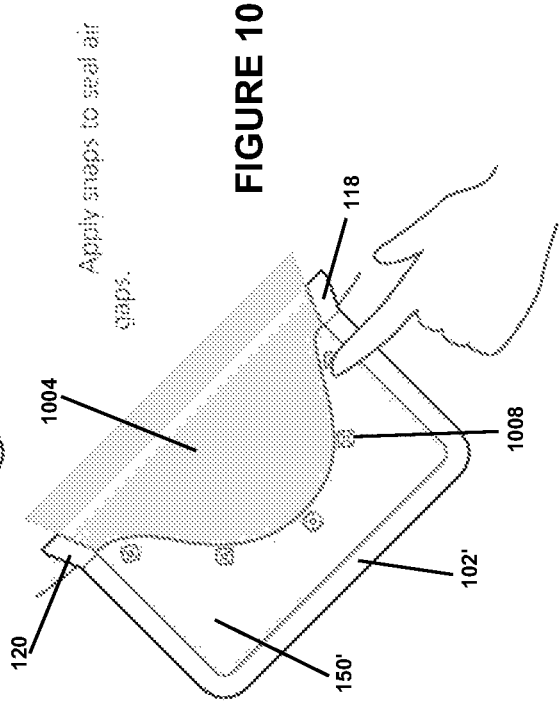

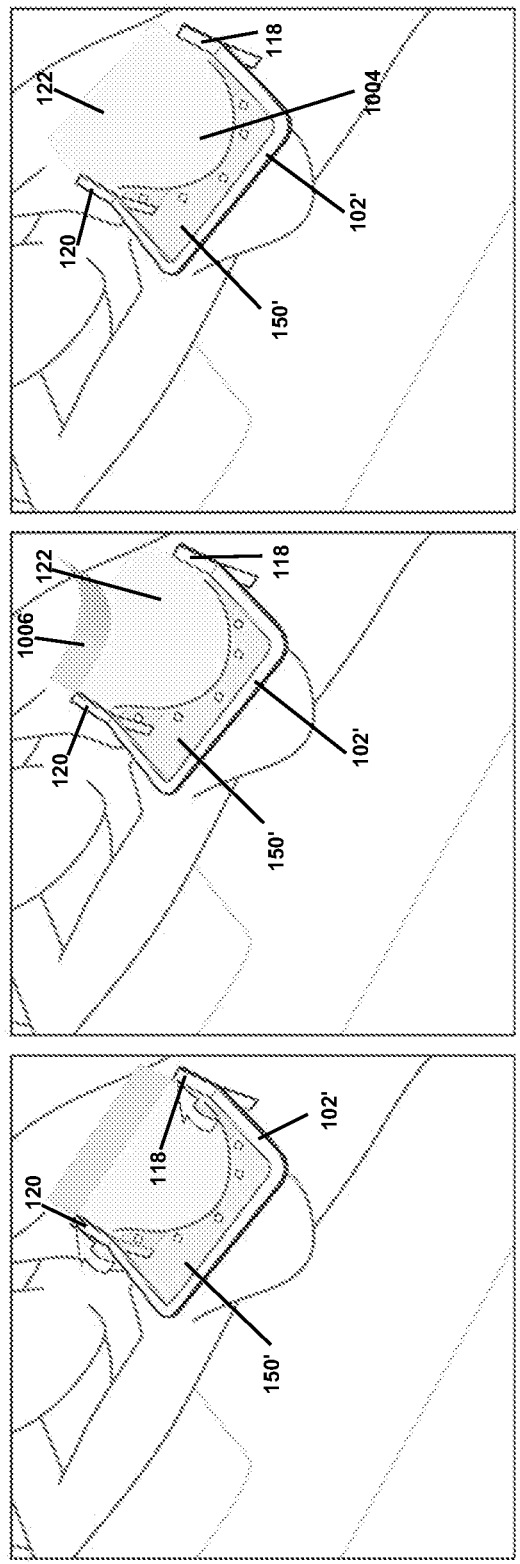

APPARATUS AND METHOD FOR SUBSTANTIALLY IMMOBILIZING A BREAST FOR MEDICAL IMAGING PROCEDURE

RELATED APPLICATIONS

This application claims priority from U.S. Provisional Application 61/272,009 filed Aug. 6, 2009, the contents of which are herein incorporated by reference.

TECHNICAL FIELD

This invention relates to tissue immobilization and stabilization for imaging procedures, and specifically relates to a breast immobilization apparatus for substantially immobilizing a breast during imaging and/or interventional procedures.

BACKGROUND

Medical imaging of breast tissue can, among other things, assist the detection and delineation of breast cancers. Various medical imaging scans, such as MRI imaging scans and/or ultrasound imaging scans, provide data for the detection of potential suspicious regions in breast tissue where an intervention, such as, for example, a biopsy may be performed.

In some imaging systems it can tend to be important that the imaging apparatus is as close as possible to the surface of the tissue being imaged. For example, in MRI imaging the closer the receiving coils are to the tissue surface, the signal-to-noise ratio tends to be improved. In another example, for ultrasound imaging, it may be important that there is direct contact or contact without airspace between an ultrasound probe and a breast tissue surface, and so it can tend to be important to have an ultrasound probe pressed directly, or as closely as possible to the tissue, or, in some examples, an ultrasound permeable material in direct contact with the tissue.

In certain immobilization apparatuses, there are two sterile compression plates, one on each of the medial and lateral sides of a patient's breast, to immobilize the breast tissue while the patient lies in the prone position. Such approaches tend to not allow the geometric relationship between the apparatus, the breast tissue and the torso of the patient to be maintained if the patient moves out of the imaging position, for example if they were to stand up and move about the imaging facility. Additionally, in such exemplary immobilization apparatuses, the compression plates frequently do not conform exactly to the shape of the breast and as such, all surfaces of the breast may not be accessible for a subsequent image, such as an ultrasound, or for delivery of an interventional instrument, such as, for example, a biopsy needle, when performing a biopsy or image-guided intervention. Additionally, these immobilization apparatuses may apply pressure on a patient's breast tissue which may cause discomfort to the patient.

It can also tend to be advantageous for improving workflow in medical imaging facilities to allow patients to easily change positions while being imaged. It may further be advantageous to allow patients to stand up and walk away from imaging systems, such as MRI systems, while immobilizing and/or stabilizing the breast in a known geometry (such as a held position and shape), and/or maintaining a fixed geometric relationship between the breast and the torso of the patient. In such applications it can be advantageous to limit the extent to which the tissue being imaged, such as a breast, may change positions or shape when a patient moves during an imaging procedure in order to maintain an approximately constant relationship between the geometry of the patient's breast and the previously acquired imaging data. Additionally, it may be desirable to be able to co-register multiple images from the same imaging systems, such as multiple MRI images acquired using different pulse sequences, or to co-register multiple images from different imaging systems, such as MRI images and ultrasound images. It may be necessary to minimize changes in the geometric position of a breast relative to the torso or relative to the immobilization device as a patient changes positions or moves to a different location in a medical imaging facility, which can tend to improve the accuracy and/or ability to co-register different images of the breast.

SUMMARY OF THE INVENTION

In an aspect of the present invention there is provided an apparatus for substantially immobilizing a breast of a patient relative to a torso of the patient, the apparatus comprising a first support member having a first and a second base each capable of engagement with the torso, the first support member defining a first inner area and when the each base is engaged with the torso the first support member extending outwardly from the first base in a path over the breast to the second base; a corresponding second support member removably engageable to the first support member the second support member defining a second inner area and when engaged to the first support member the first and second inner areas in substantial alignment; a first and a second deformable membrane, the first deformable membrane removably connected to the first support member substantially covering the first inner area and the second deformable membrane removably connected to the second support member substantially covering the second inner area, the first and second membranes defining a pocket that can receive the breast as the second member is moved from the open position to the closed position, to substantially immobilize the breast relative to the torso of the patient.

The apparatus may further comprise a locking mechanism capable of locking the second support member to the first support member, when each base is engaged with the torso.

The first and second membranes may be non-magnetic and acoustically permeable. Additionally, each of the first and second membranes may have a surface having an adhesive for adherence to at least one of the breast and the adhesive surface of the other of the membranes. Additionally, the bases may be flexible to conform to the torso of the patient. Additionally, the second base may be hingedly connected to the first support member capable of engagement with a side of the torso of the patient.

The membranes may be connected to an extended membrane portion having an adhesive surface capable of removable adherence to the torso of the patient.

In some aspects of the present invention, fiducial markers may be engaged to at least one of the first and second support members which may tend to provide reference markers during subsequent imaging.

The apparatus may further comprise a chest support member connected to the first and second bases capable of engagement with the torso.

In another aspect of the present invention there is provided an apparatus for substantially immobilizing a breast of a patient relative to a torso of the patient, the apparatus comprising a first support member having a first and a second base each capable of engagement with the torso, the first support member defining a first inner area and when the each base is engaged with the torso the first support member extending outwardly from the first base in a path over the breast to the second base; a corresponding second support member removably hinged to the first support member such that the first and second members may be movable between an open and closed position, the second support member defining a second inner area and when engaged to the first support member the first and second inner areas may be in substantial alignment, when the members are in the closed position; a first and a second deformable membrane, the first deformable membrane removably connected to the first support member substantially covering the first inner area and the second deformable membrane removably connected to the second support member substantially covering the second inner area, the first and second membranes defining a pocket that can receive the breast as the second member is moved from the open position to the closed position, to substantially immobilize the breast relative to the torso.

The apparatus may further comprise a locking mechanism capable of locking the second support member to the first support member, when each base is engaged with the torso The first and second membranes may be non-magnetic and acoustically permeable. Additionally, the first and second membranes may have a surface having an adhesive for adherence to at least one of the breast and the adhesive surface of the other of the membranes. Additionally, the bases may be flexible to conform to the torso of the patient. Additionally, the second base may be hingedly connected to the first support member capable of engagement with a side of the torso of the patient.

The membranes may be connected to an extended membrane portion having an adhesive surface capable of removable adherence to the torso of the patient.

In some aspects of the present invention, fiducial markers may be engaged to at least one of the first and second support members which may tend to provide reference markers during subsequent imaging.

The apparatus may further comprise a chest support member connected to the first and second bases capable of engagement with the torso.

In a further aspect of the present invention there is provided an apparatus for substantially immobilizing a breast of a patient relative to a torso of the patient, the apparatus comprising a breast support and a harness, the breast support comprising a first support member defining a first inner area; a corresponding second support member defining a second inner area, removably hinged to the first support member, such that the first and second members can move between an open and closed position, the second support member defining a second inner area and when engaged to the first support member the first and second inner areas may be in substantial alignment when the members are in the closed position, a first and a second deformable membrane, the first deformable membrane removably connected to the first support member substantially covering the first inner area and the second deformable membrane removably connected to the second support member substantially covering the second inner area, the first and second membranes can define a pocket to receive the breast as the second member is moved from the open position to the closed position, to substantially immobilize the breast relative to the torso of the patient; and the harness comprising a sternum support capable of engagement with the torso substantially along the sternum of the patient; a first and a second support engagement member extending from the sternum support towards the breast, the first support member coupled to the first and second support engagement members and extending outwardly from the first support engagement member in a path over the breast to the second support engagement member; and an adjustable strap connected to the sternum support capable of securing the patient to the sternum support.

The apparatus may further comprise a locking mechanism capable of locking the second support member to the first support member, when each base is engaged with the torso.

The first and second membranes may be non-magnetic and acoustically permeable. Additionally, the first and second membranes may have an adhesive surface for adherence to at least one of the breast and the adhesive surface of the corresponding membrane.

The membranes may be connected to an extended membrane portion having an adhesive surface capable of removable adherence to the torso of the patient.

In some aspects of the present invention, fiducial markers may be engaged to at least one of the first and second support members which may tend to provide reference markers during subsequent imaging.

The apparatus may additionally comprise a corresponding second breast support coupled to the sternum support capable of substantially immobilizing a second breast of the patient.

In a further aspect of the present invention there is provided methods for obtaining a medical image of a tissue of interest of a patient, the method comprising the steps of: substantially immobilizing the breast of a patient relative to a torso of the patient with a portable immobilization device; performing a first imaging scan of the breast to obtain a first medical image with a first imaging system; re-positioning the patient, the breast of the patient remaining substantially immobilized in the immobilization device; and performing a second imaging scan to obtain a second medical image with a second imaging system.

The method may additionally comprise the steps of connecting a fiducial marker to the immobilization device, the fiducial marker detectable by at least one of the first imaging scan and the second imaging scan; and co-registering the first medical image with the second medical image. Additionally, in some embodiments, the immobilization device can be installed on the patient so as to secure the breast in a pocket formed between two flexible membranes which are non-magnetic and acoustically permeable, and the first imaging scan can be an MRI imaging scan and the second imaging scan can be an ultrasound imaging scan.

BRIEF DESCRIPTION OF THE DRAWINGS

For a better understanding of embodiments of the system and methods described herein, and to show more clearly how they may be carried into effect, reference will be made by way of example, to the accompanying drawings in which:

FIGS. 10A-10J show a work flow of a method for substantially immobilizing a breast of a patient

DETAILED DESCRIPTION

Figure 1:
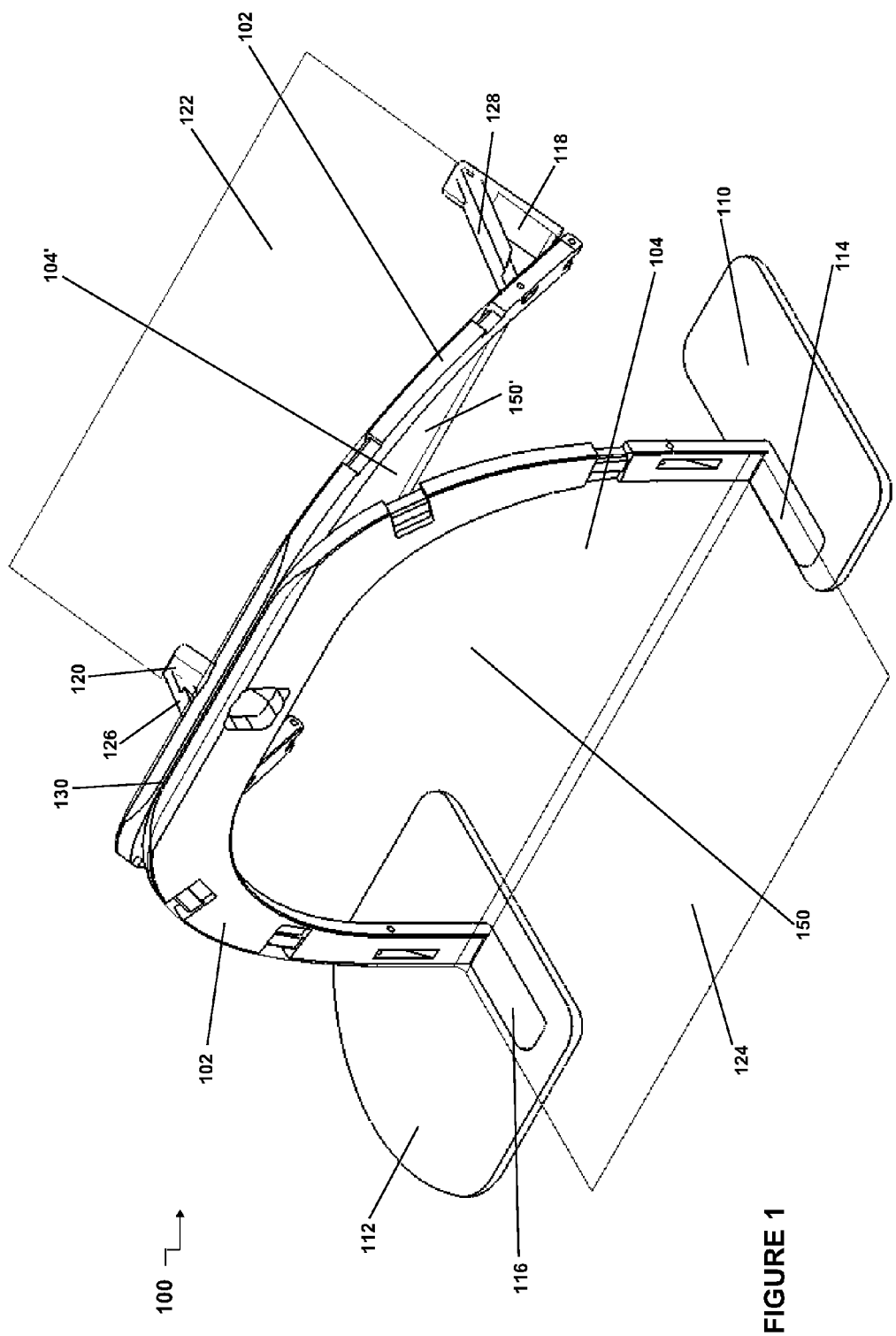
FIG. 1 shows a front isometric view of an apparatus for substantially immobilizing a breast of a patient.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein. For ease of reference, certain reference numerals are reused when referring to similar elements even among different embodiments. Additionally, it will be appreciated that the various embodiments are operative with actual persons and tissues, including breasts.

Figure 3:
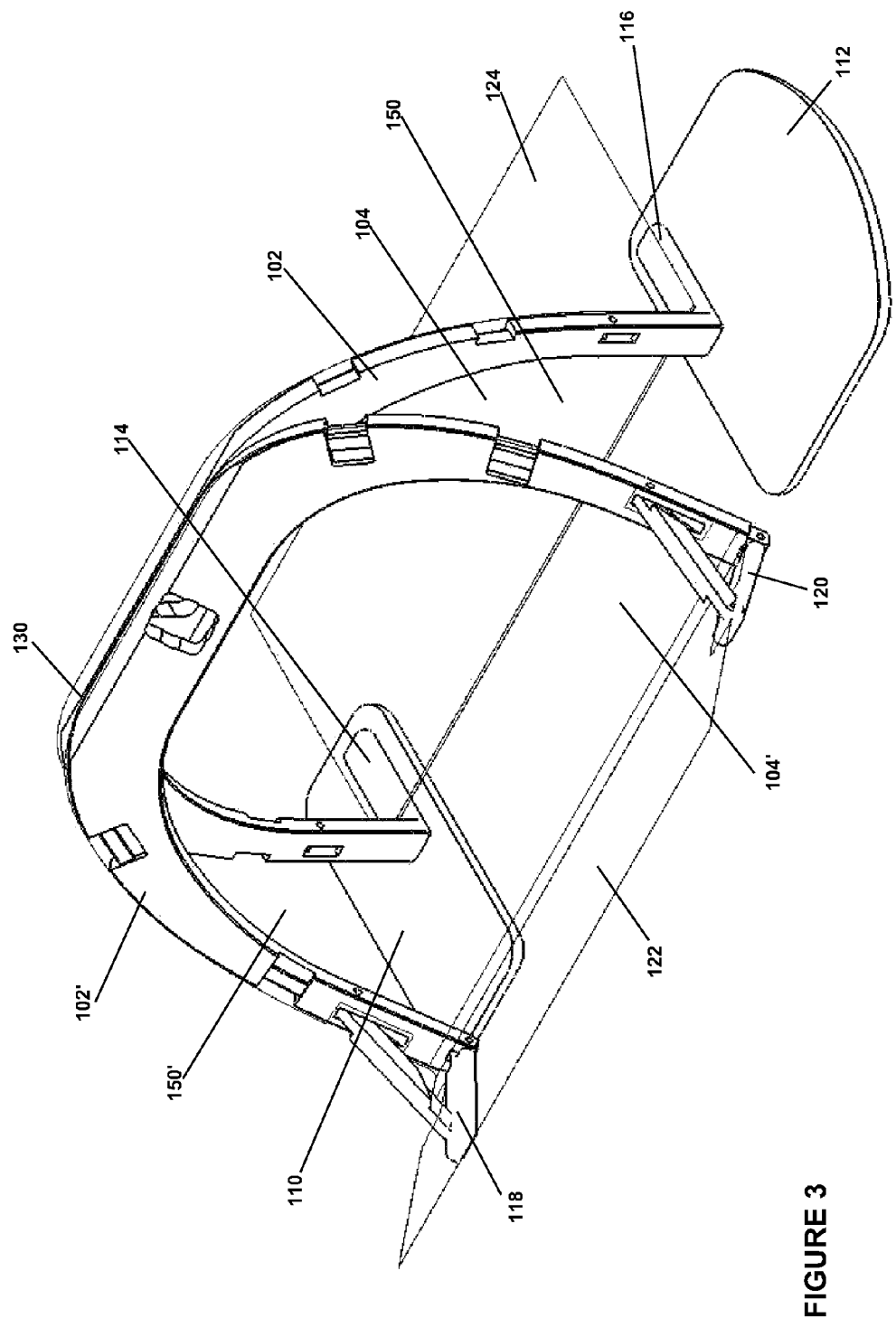
FIG. 3 shows a back isometric view of the apparatus of FIG. 1.

With reference to FIGS. 1 and 3, apparatus 100 is shown. Apparatus 100 as shown has two corresponding support members 102 and 102'. Support member 102 defines inner area 104 and support member 102' defines corresponding inner area 104'. Support member 102 can be connected to bases 110 and 112 and can extend outwardly from base 110 such that when in use support member 102 defines a path over the breast to base 112.

Support members 102 and 102' may be constructed from a non-magnetic material tending to reduce interference with an MRI scanner. In some embodiments, support members 102 and 102' can be made from epoxy-glass laminate, polyetherimide, for example Ultem™ manufactured by SABIC, glass filled polyetherimide, polyphenylene sulphide, glass filled polyphenylene sulphide, Radel™ manufactured by Solvay Advanced Polymers, polyaryletheretherketone, glass filled polyaryletheretherketone, polycarbonate or glass filled polycarbonate.

Bases 110 and 112 may tend to provide pressure against the torso of a patient, in some embodiments the front of the torso of patient, when apparatus 100 is in use which may tend to provide support for apparatus 100 for substantially immobilizing the breast of the patient relative to the torso. In some embodiments, bases 110 and 112 may be constructed of a flexible material, such as a flexible plastic, which may tend to conform to the shape of the torso of a patient when bases 110 and 112 are engaged with the torso of the patient, in some embodiments on the front of the torso proximate the breast, one of bases 110 and 112 above the breast and the other below the breast. Additionally, the use of a flexible material for bases 110 and 112 may tend to increase patient comfort. In some alternative embodiments, bases 110 and 112 may be connected by an additional sternum support member tending to provide additional support for apparatus 100 against the torso of a patient when apparatus 100 is in use proximate to the sternum of the patient.

Bases 110 and 112 may be integral to support member 102 and in some alternative embodiments, support member 102 may have outwardly extending feet 114 and 116 which may be connected to bases 110 and 112. Outwardly extending feet 114 and 116 tending to provide additional support for apparatus 100 when in use.

In some embodiments, bases 110 and 112 may be hingedly connected to support member 102, such hinged connection tending to allow bases 110 and 112 to be positioned along the contour of the torso of a patient and may tend to allow support member 102 to extend generally perpendicular to the front of the torso of a patient when apparatus 100 is in use. Additionally, such hinged connection may tend to prevent rotation of support member about the superior-inferior axis of the patient. The hinged connection of bases 110 and 112 to support member 102 may be a biased spring and in some embodiments a locking mechanism may be provided tending to lock the hinged connection in place.

Support member 102' may, in some embodiments, have additional support feet members 118 and 120 outwardly extending from support member 102' which may engage bases 110 and 112 tending to provide additional support for apparatus 100 when apparatus 100 is in use to substantially immobilize the breast of a patient. Support feet members 118 and 120 may be pivotally connected to support member 102' by pins, rotateable about the longitudinal axis of the pins and in some embodiments a locking means may be provided tending to hold support feet members 118 and 120 in a fixed position.

Additionally, in some embodiments, angled members 126 and 128 may be connected to support feet members 118 and 120 tending provide additional support for apparatus 100. Such angled members 126 and 128 may tend to prevent unwanted rotation of support feet member 118 and 120 about the superior-inferior axis.

Deformable membrane 150 can be connected across inner area 104 of support member 102 and corresponding deformable membrane 150' can be connected across inner area 104' of support member 102'. Deformable membranes 150 and 150' may be constructed of a material that is non-magnetic and acoustically permeable, which may tend to prevent interference with MRI imaging and ultrasound imaging when in use.

In some embodiments, deformable membranes 150 and 150' may have a magnetic permeability that will tend not to distort the homogeneity of an MRI's magnetic field more than 1 ppm. Additionally, in some embodiments, deformable membranes 150 and 150' may have an acoustic impedance less than 4 megarayleighs and additionally may have a thickness of less than $\frac{1}{12}$ of the wavelength of a 14 MHz ultrasound transducer in water with an attenuation less than 3 dB. In some embodiments, deformable membranes 150 and 150' may additionally be substantially optically transparent. In some embodiments, deformable membranes 150 and 150' can partially cover inner area 104 and 104', providing gaps, holes or openings, in such embodiments deformable membranes 150 and 150' may not be acoustically permeable, allowing ultrasound imaging to be performed through the gaps, holes or openings.

Support members 102 and 102' may be hingedly connected by hinged connection 130 along the upper portion of support members. Hinged connection 130 may tend to provide a means to align support members 102 and 102' when in use, as apparatus 100 is transitioned from an open to a closed position, the closed position tending to be the position in which apparatus 100 is substantially immobilizing a breast of a patient. Persons of skill will understand that other alignment means may be used to provide alignment for support members 102 and 102' when apparatus 100 is in use, such that a breast is substantially immobilized by apparatus 100 between deformable membranes 150 and 150'.

Figure 4A:
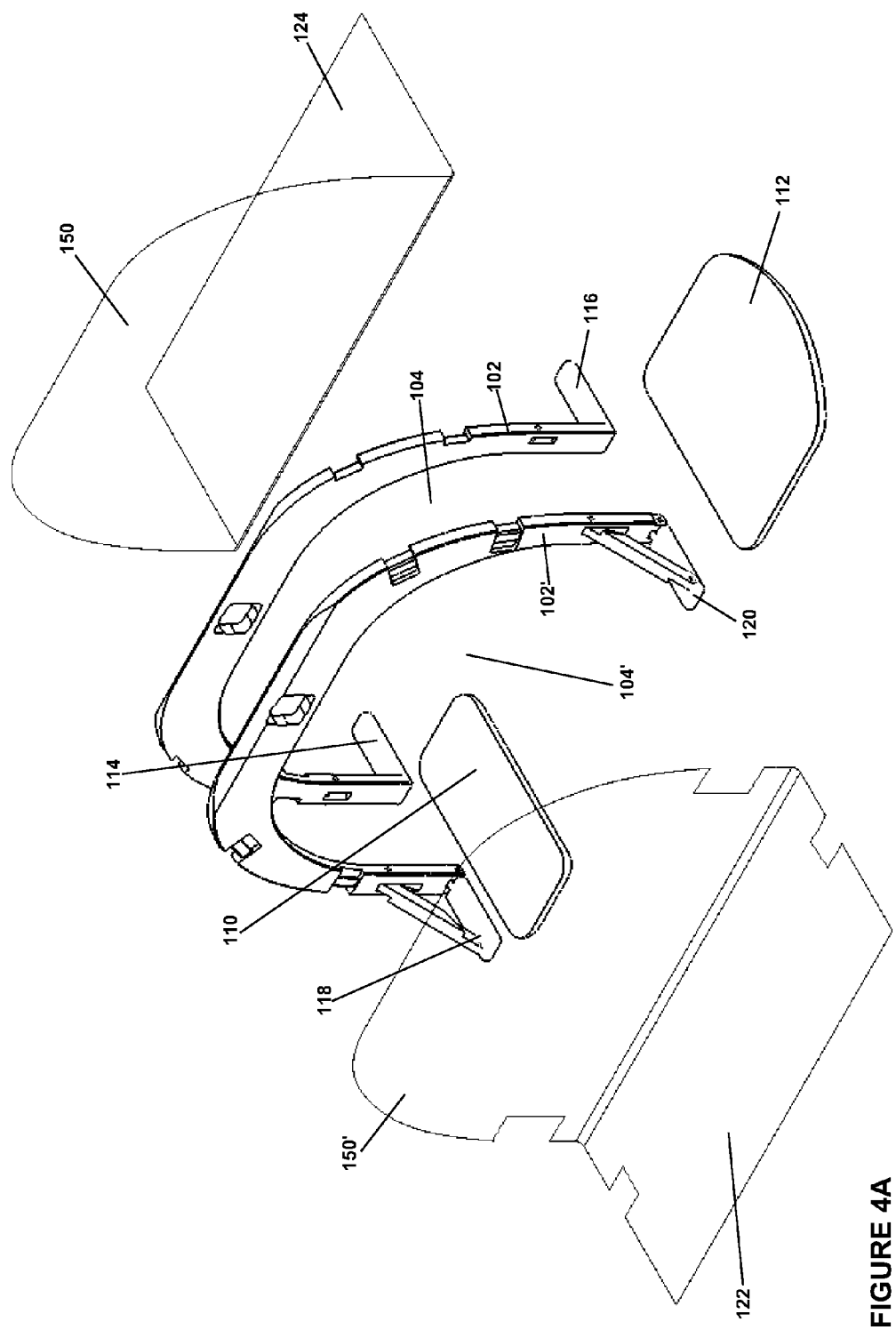
FIG. 4A shows an exploded view of the apparatus of FIG. 1.

In other embodiments, support members 102 and 102' may be separate components tending to be aligned by a user. For example, with reference to FIG. 4A, an exploded view of apparatus 100 is shown, this apparatus not having any hinged connection. Such apparatus may be constructed by positioning membranes 150 and 150' onto respective support members 102 and 102' and additionally connecting bases 110 and 112 to feet supports 114 and 116. Support member 102 may be connected to support member 102' around the breast of a patient such that a pocket is formed by membranes 150 and 150' around the breast of a patient. Support members 102 and 102' may be held in position relative to each other by a locking member, such as a clip, that may tend to prevent unwanted relative movement between support members 102 and 102'.

Referring again to FIGS. 1 and 3, when in use, support members 102 and 102' may be connected together around a tissue, such as a breast, wherein deformable membranes 150 and 150' form a pocket to receive the breast, the pocket being formed as support members 102 and 102' are moved into a closed position around the breast. In the closed position, deformable membranes 150 and 150' tend to press against a patient's breast so as to immobilize the breast and maintain a substantially fixed geometric shape of the breast, and also to substantially maintain the position of the breast relative to the patient's torso.

Additionally, deformable membranes 150 and 150', may tend to substantially maintain breast tissue away from the torso of a patient. As such, support member 102 when engaged with corresponding support member 102' may tend to provide support tending to allow a patient to be repositioned, such as from a prone position to a supine position, and/or to stand up and move around an imaging facility between imaging sessions while substantially immobilizing the breast, maintaining a substantially fixed geometric relationship between the patient's breast and the patient's torso.

In some embodiments one, or both, of the surfaces of deformable membranes 150 and 150' may have an adhesive so as to be able to adhere to objects, such as tissue, for example, a breast, to be examined, or the other corresponding deformable membrane 150 or 150' on the corresponding support member 102 or 102'. As an example, an inner surface of deformable membranes 150 and 150' may be similar to sticky tape. In such embodiments, deformable membranes 150 and 150' may adhere to each other when in contact with one another which, when in use, may tend to further resist motion and deformation of the breast. Deformable membranes 150 and 150' may be stretchable, either elastically or plastically, as well as flexible, which may tend to allow deformable membranes 150 and 150' to conform to non-planar and non-prismatic areas of the breast. Deformable membranes 150 and 150' may additionally include a region of increased thickness, which may tend to resist stretching of deformable membranes 150 and 150' in the area of increased thickness. In some embodiments, when in use, the area of increased thickness may tend to be located near the torso and may tend to provide additional support for apparatus 100.

In some embodiments deformable membranes 150 and 150' may be made from a film from the family of wound stabilizing adhesive-backed membranes made by 3M and/or Smith and Nephew. Additionally, deformable membranes 150 and 150' may have a biocompatible adhesive and film, which may tend to reduce skin trauma or residue when deformable membranes 150 and 150' are removed from contact with tissue. Additionally, deformable membranes 150 and 150' may be permanently deformable in two or more directions when pressed against a tissue, such as a breast.

Deformable membranes 150 and 150' may be connected to corresponding support members 102 and 102' such that when in use, deformable membranes 150 and 150' are flush with the surface of corresponding support members 102 and 102' that is closest to the breast of a patient. Such positioning of deformable membranes 150 and 150' may tend to prevent air pockets from forming between such deformable membranes 150 and 150' when pressed against the breast of a patient when support members 102 and 102' are connected around the breast of a patient. Additionally, the connection of snaps applied to the outer surfaces and connected through deformable membranes 150 and 150' and applied over the region of any air pocket may tend to minimize the effect such air pocket may have on imaging. A first connection member of the snap may be positioned on the exterior surface of deformable membrane 150 against an air pocket and the first connection member of the snap may be engaged with the second connection member, engaged with the exterior surface of deformable membrane 150', tending to trap membranes 150 and 150' within the snap.

In embodiments in which one or both of the deformable membranes 150 and 150' are adhesive, such deformable membranes 150 and 150' will tend to stick to the breast of a patient and the torso and/or the other corresponding deformable membrane 150 and 150' so that air pocked will tend to be minimized, especially along the surface of the breast of a patient. The minimization of air pockets can tend to be advantageous in applications, such as, for example, those involving ultrasound probes in which solid contact (i.e., probe touching membrane touching tissue, without air between the membrane and tissue or between the probe and membrane) tends to be desirable.

Figure 2:
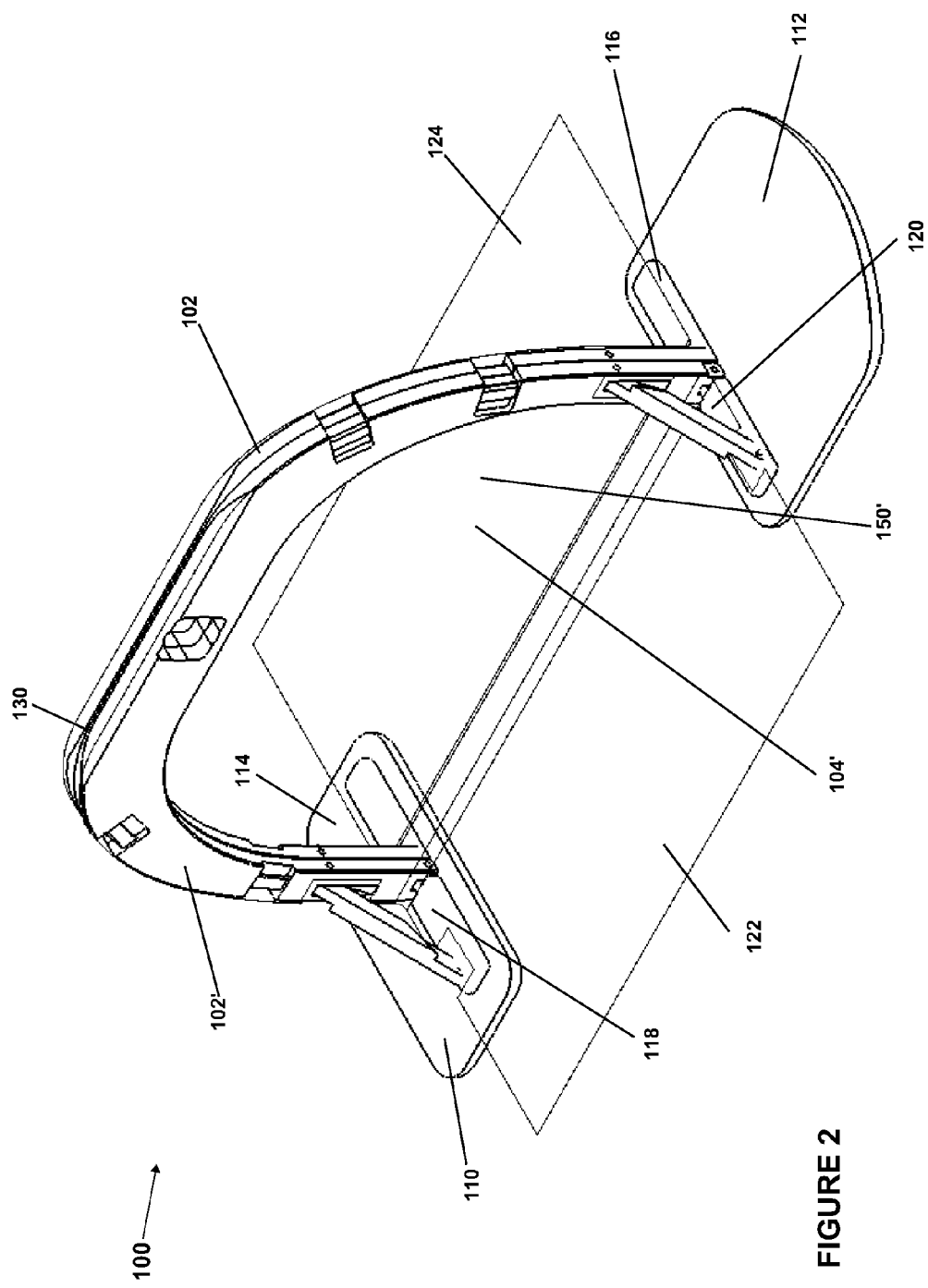
FIG. 2 shows an isometric view of the apparatus of FIG. 1 in a closed position.

When support members 102 and 102' are connected together around the breast of a patient, as described above, apparatus 100 may appear as shown in FIG. 2 (breast not shown). Therein, support members 102 and 102' are pressed against one another and may be held together relative to each other by a locking means, for example a clip, and deformable membranes 150 and 150' may tend to be pressed against one another, tending to immobilize and/or stabilize a breast relative to the torso of a patient.

Support members 102 and 102' may also have notches for receiving removable connection mechanisms tending to hold corresponding support members 102 and 102' together, relative to each other, when in use, tending to prevent unwanted sliding of support members 102 and 102' relative to each other.

The adhesive nature of deformable membranes 150 and 150' can also be advantageous in sticking to the torso of a patient so as to provide additional immobilization and/or stabilization of the breast of a patient relative to the torso. In some embodiments, extended membrane portions 124 and 122 may be connected to the corresponding deformable membrane 150 and 150' extending outwardly and capable of engagement with the torso tending to provide additional support for apparatus 100.

Figure 4B:
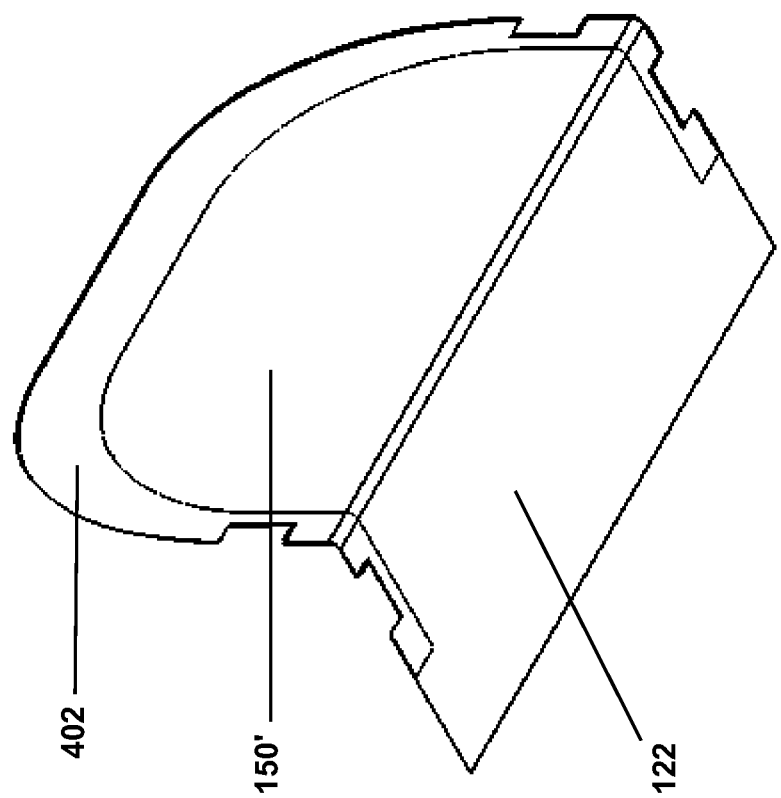
FIG. 4B shows an isometric view of an embodiment of a membrane support structure.

With additional reference to FIG. 4B, in some embodiments, deformable membranes 150' may be connected to membrane support structure 402. In such embodiments, support member 102' may be connectable to a corresponding membrane support structure 402 such that the deformable membrane 150' may substantially cover the inner area 104'. Membrane support structure 402 may be connected to support member 102' by a groove or a clip which may be integral to the respective support member 102'. In some embodiments, membrane support structure 402 may be a disposable portion of apparatus 100 where, when in use, sterile membrane support structure 402 may be used and disposed of after imaging sessions and/or interventional procedures are completed and support member 102' may be a reusable portion of apparatus 100. Persons of skill will understand that a corresponding membrane support structure having deformable membrane 150 substantially covering inner area 104 may be comprised of substantially similar elements operating in a substantially similar manner as that membrane support structure 402.

In some embodiments, position markers, such as fiducial markers, may be affixed to support members 102 and 102'. Position markers may tend to allow for images acquired with an initial imaging system, such as an MRI system, to be registered to images acquired from a subsequent imaging system, such as an ultrasound imaging system, via the known geometric relationship between the position markers, apparatus 100 and the tissue being imaged. In such embodiments, position markers, such as fiducial markers, may be visible to imaging systems and/or tracking systems, which may monitor the location and orientation of imaging equipment, such as, for example, a handheld ultrasound probe. It will be understood by those of skill in the art that position markers may be connected to any convenient element of apparatus 100.

In some embodiments, position markers may be a retro-reflective dot, sphere or hemisphere, a resonant coil, an active laser, an LED light source, a radio transmitter, a radioactive pellet, an MRI fiducial, such as PinPoint™ or MR-SPOTS™ Multi-Modality Fiducial Markers by Beekley Corporation, and/or any fluid filled vessel containing between 0.5 mL and 10 mL of fluid having T1 and T2 characteristics which may tend to provide visibility on clinical MRI images. In other embodiments RF magnetic tracking may be employed, and appropriate RF sensors can be connected to any suitable location on apparatus 100. In other embodiments, position markers may be CT or X-Ray visible. In some embodiments, position markers may be one or more retro-reflective spheres, MRI or PET-visible fluid-filled vials, or magnetic position tracking coils. Additionally, or alternatively, position markers may be one or more fiber-optic trackers, such as, for example, ShapeTape™, manufactured by Measurand, Inc.

Support members 102 and 102' may receive position markers in fixed locations, for example a position marker may have an engagement projection and support members 102 and 102' may have a corresponding receiving slot tending to secure a position marker in a fixed location. Such embodiments may tend to provide consistent locations for position markers, if position markers need to be replaced during imaging, for example, with a different position marker appropriate for the current imaging. The securing of position markers to support members 102 and 102' may additionally tend to prevent undesired movements of position markers during imaging or when a patient changes positions, for example from the prone to the supine position while apparatus 100 is in use.

Support members 102 and 102' may additionally have physical landmarks integral to support member 102 and 102', such as, for example, divots or projections, which may be used by tracking devices, for example a tracked stylus, as a reference position for calibration of a tracking system. In use, a tracked stylus may be positioned in such divots or by touching such projections and its position may be registered, enabling image registration wherein the registered position marker may be the reference point as opposed to a receiver or tracking camera in other tracking systems. In other embodiments, fiducial markers may have divots or projections thereon, for example in fiducial markers tending to be doughnut shaped may have an inner divot. In such other embodiments the divot in the fiducial marker may similarly enable image registration through the use of a tracking device, such as a tracked stylus.

In other embodiments, reference markers may be drawn on support members 102 and 102', or may be drawn on deformable membrane 150 or 150', and in some embodiments may be drawn on the tissue of the patient, such as a breast, using apparatus 100. Such references may be used by tracking devices to register a reference point.

Figure 11A:
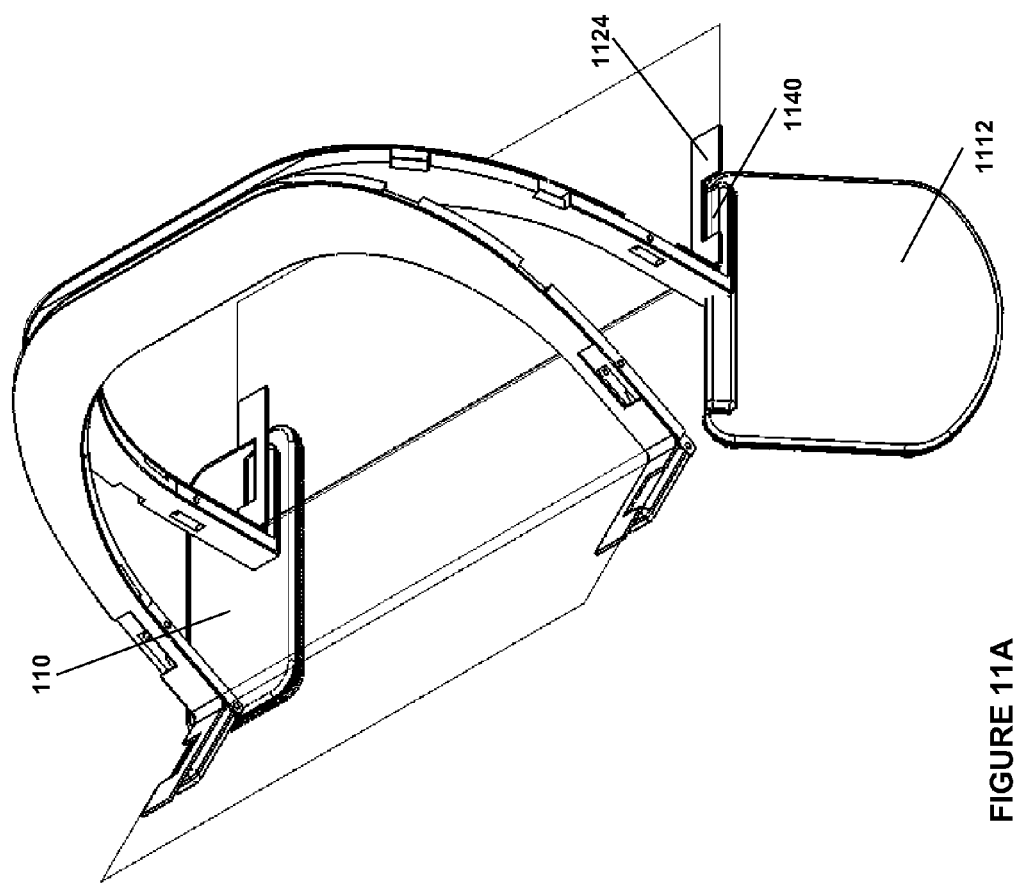
FIGS. 11A and 11B show an alternative embodiment of an apparatus for substantially immobilizing a breast of a patient.
Figure 11B:
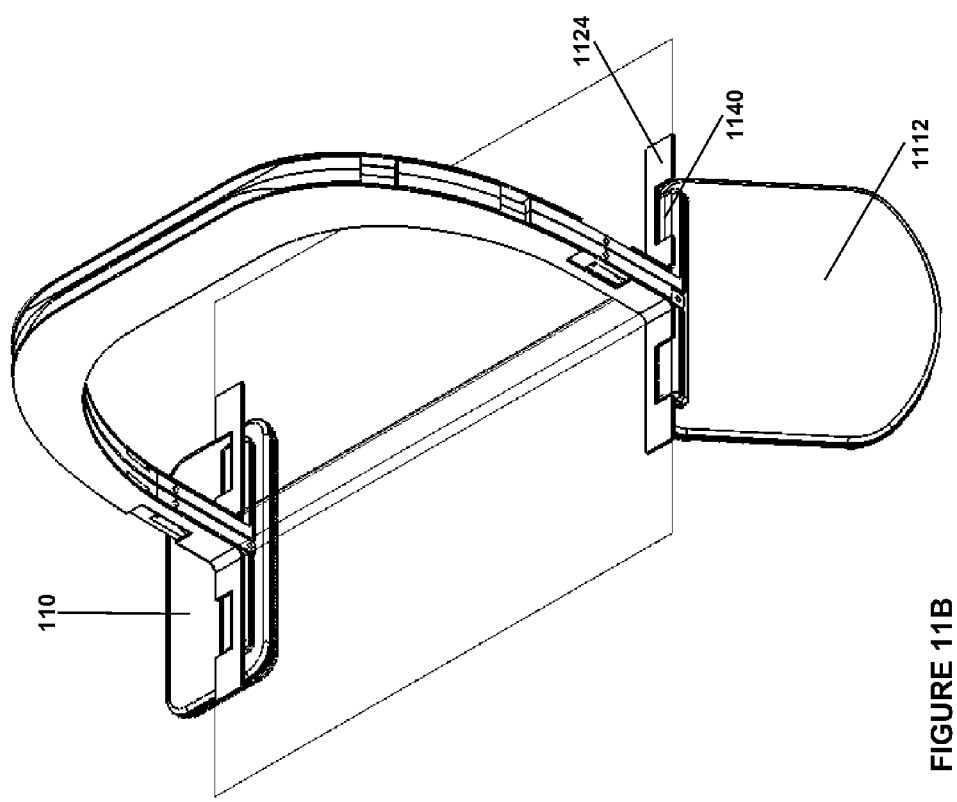

With reference to FIGS. 11A and 11B, an alternative embodiment of the invention is shown having base 1112 connected to outwardly extending foot 1124 by hinged connection 1140, such alternative embodiment of the invention for substantially immobilizing a breast of a patient relative to a torso of the patient. Base 1112 may rotate about the axis of hinged connection 1140 for engagement with the side of the torso of a patient, base 1112 tending to provide pressure against the side of the torso of the patient when in use. Additionally, a locking means may be provided to prevent unwanted rotation of base 1112 about hinged connection 1140. Base 1112 may be constructed of a flexible material, such as a flexible plastic, which may tend to conform to the shape of the side of the torso of the patient when bases 110 and 1112 are engaged with the torso of the patient. Additionally, the use of a flexible material for base 1112 may tend to increase patient comfort when bases 110 and 1112 are engaged with the torso of the patient.

Figure 12:
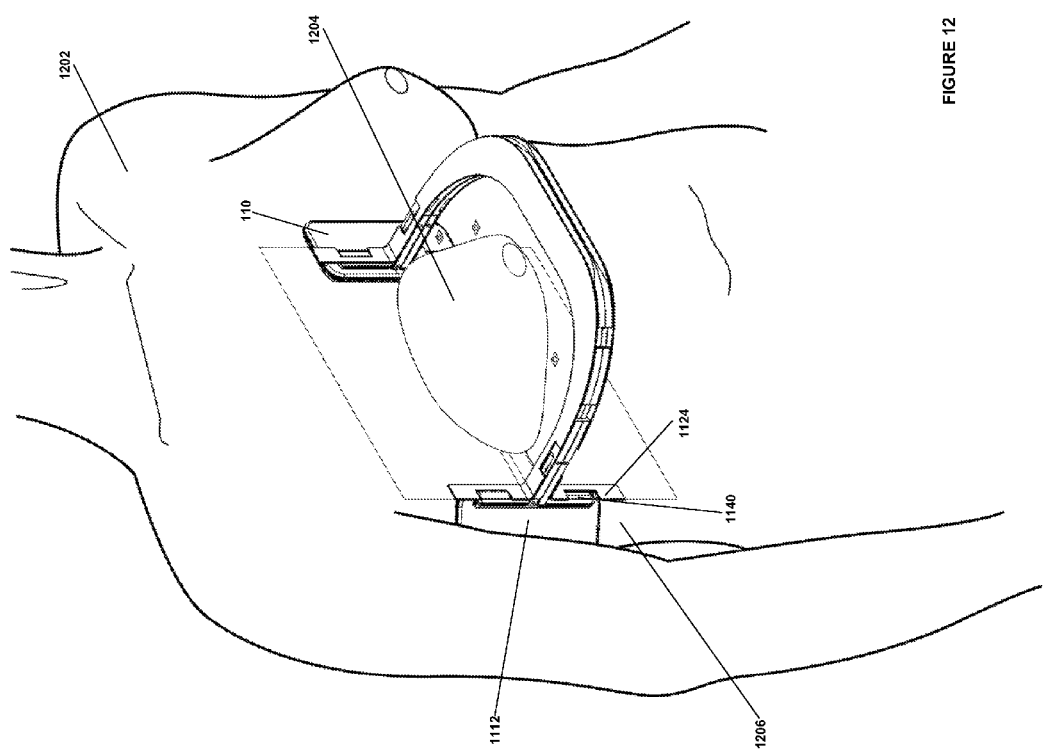
FIG. 12 shows the embodiment of FIGS. 11A and 11B substantially immobilizing a breast of a patient.

With further reference to FIG. 12, such alternative embodiment of the invention is shown substantially immobilizing breast 1204 of patient 1202, base 1112 engaged with side 1206 of the torso of patient 1202 and base 110 engaged with front of the torso of the patient, base 110 tending to be positioned proximate to the sternum of the patient. Such embodiments may substantially immobilize the breast of a patient relative to the torso of the patient by positioning the apparatus to compress and/or engage the breast in the craniocaudal direction, tending to be useful in mammography medical imaging procedures.

Figure 5:
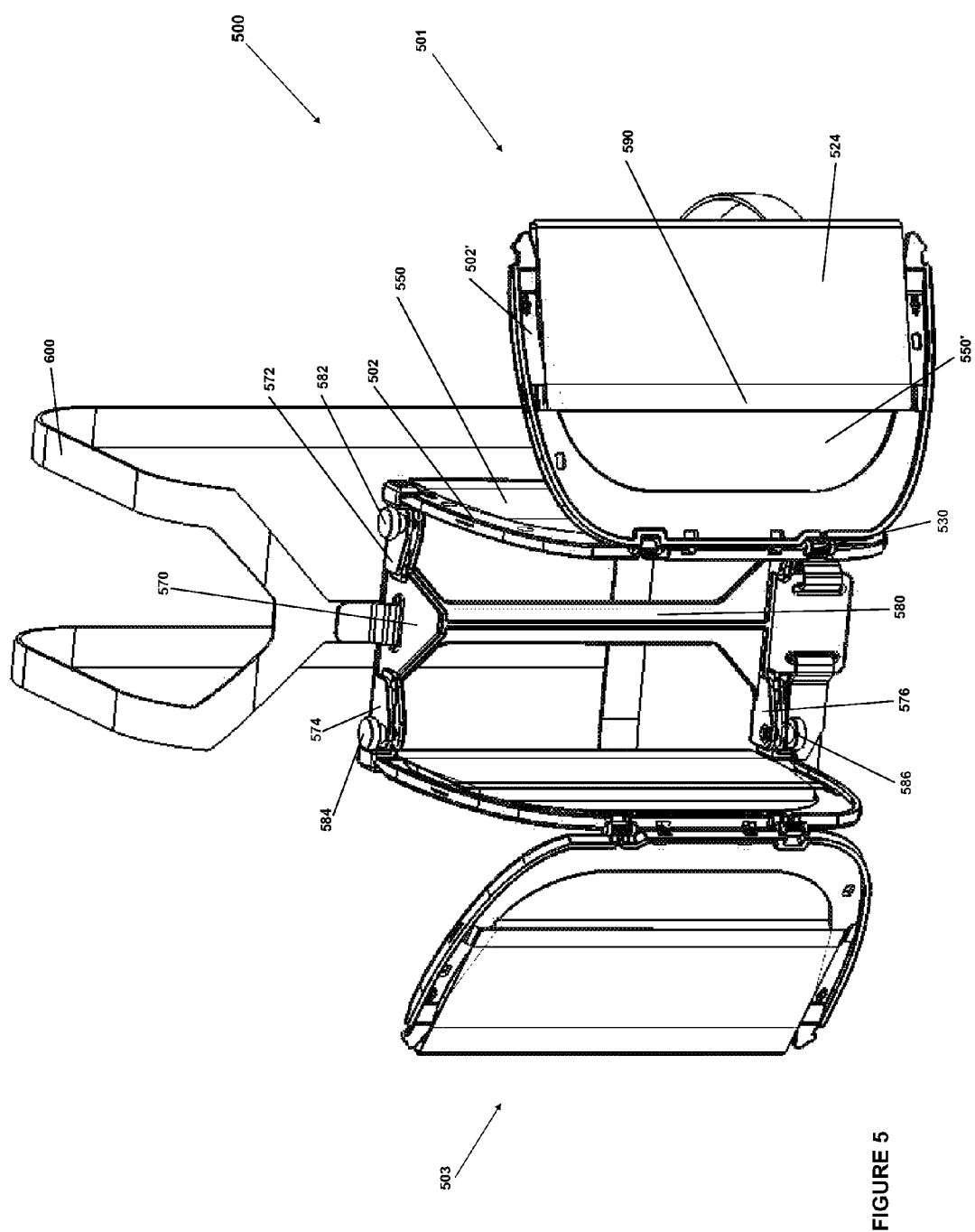
FIG. 5 shows an isometric view of alternative embodiment of an apparatus for substantially immobilizing a breast of a patient.
Figure 6:
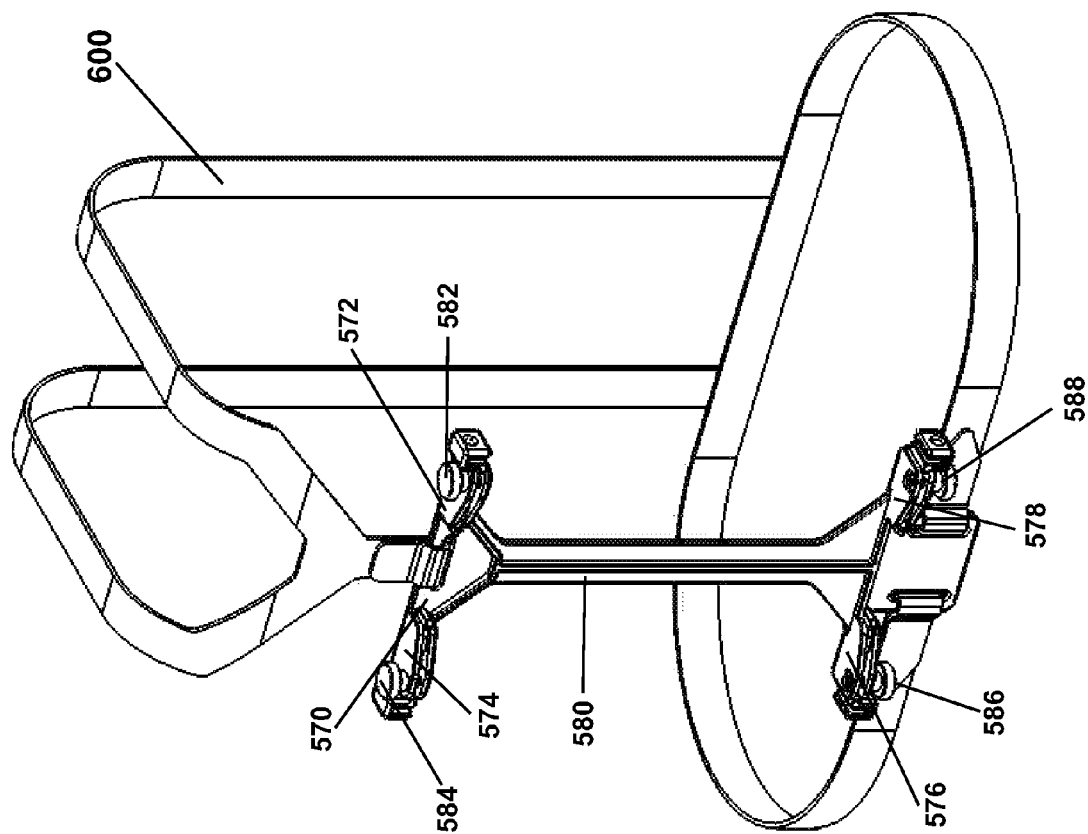
FIG. 6 shows an isometric view of a harness and sternum support of the apparatus of FIG. 5.

With reference to FIGS. 5 and 6, apparatus 500 for substantially immobilizing one or both breasts of a patient relative to a torso of the patient is shown. Apparatus 500 has harness 600 for securing apparatus 500 around the torso of a patient, such harness 600 tending to be adjustable for comfortable securing of apparatus 500 to the patient.

Harness 600 may be connected to sternum support member 570, where, when in use, sternum support member 570 tends to be positioned on the torso of the patient along the sternum of the patient. Sternum support member 570 may tend to provide pressure against the torso of a patient which may tend to provide support for apparatus 500 when in use. In some embodiments, sternum support member 570 may be constructed of a flexible material, such as a flexible plastic, which may tend to conform to the shape of the torso of a patient tending to increase patient comfort and improve support.

Breast immobilization apparatus 501 and 503 may be engaged with sternum support member 570, which, when in use, may tend to substantially immobilize the breasts of a patient. Persons of skill will understand that apparatus 500 may immobilize one or both breasts of a patient and if it is desired to immobilize only the left breast of a patient that breast immobilization apparatus 503 may be removed and if it is desired to immobilize only the right breast of a patient that breast immobilization apparatus 501 may be removed.

Breast immobilization apparatus 501 may comprise support member 502 and corresponding support member 502', each defining an inner area. Deformable membrane 550 may be connected across the inner area defined by support member 502 and corresponding deformable membrane 550' may be connected across the inner area defined by support member 502'. Support members 502 and 502' can be hingedly connected such that, when in use, breast immobilization apparatus 501 may be transitioned from an open position to a closed position, the closed position tending to be the position in which breast immobilization apparatus 501 tends to substantially immobilize a breast. Persons of skill will additionally understand that breast immobilization apparatus 503 is substantially similar to breast immobilization apparatus 501.

Figure 7:
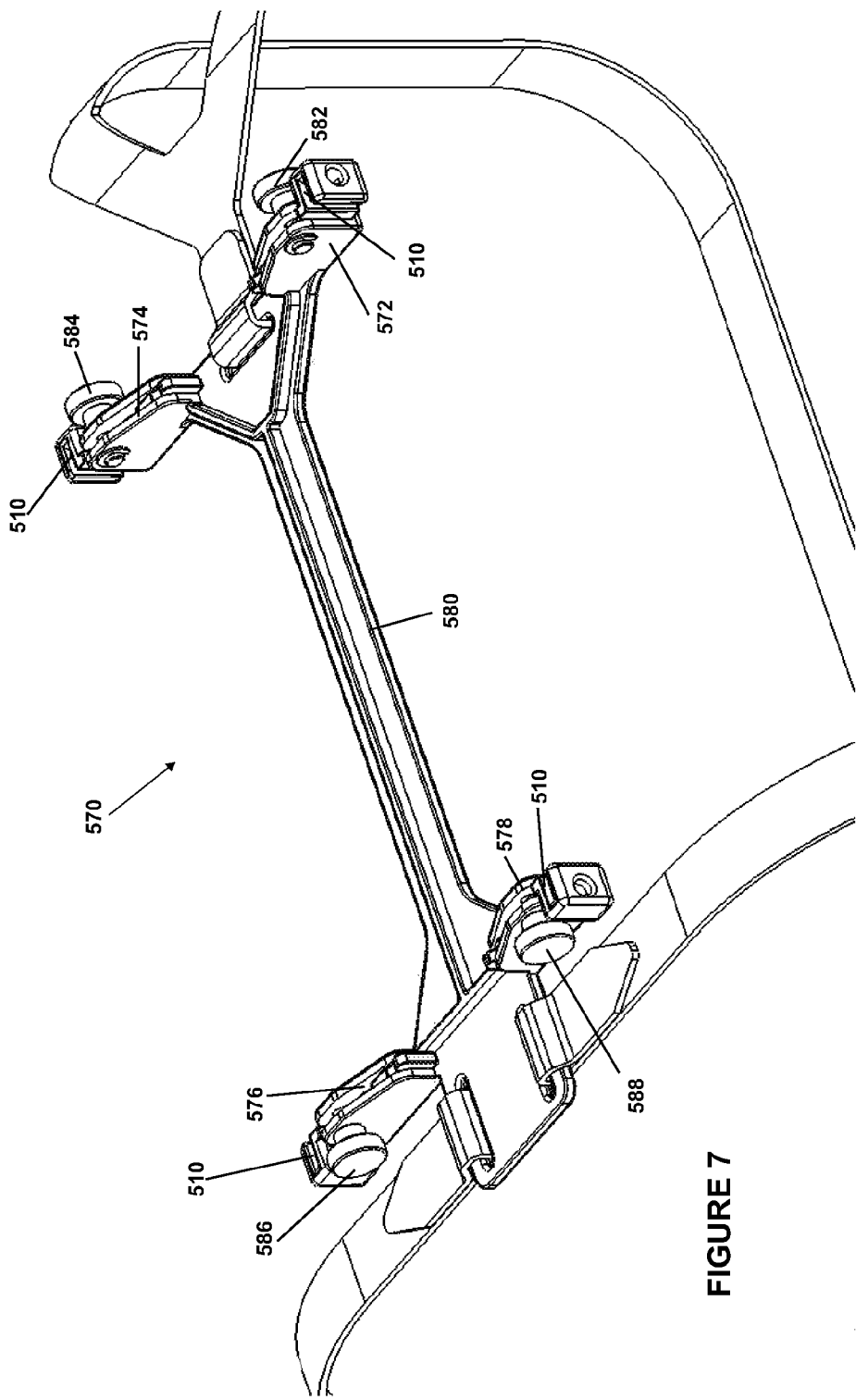
FIG. 7 shows an isometric close-up of the sternum support of the apparatus of FIG. 5.

With additional reference to FIG. 7, sternum support member 570 may have central support 580 having additional support engagements 572 and 578 extending therefrom, laterally along the torso of the patient when in use. Support engagements 572 and 578 may engage support member 502 and may, in some embodiments, be comprised of slots 510 for slideable engagement with support member 502 having corresponding projections for insertion into the slots.

Support engagements 572 and 578 may additionally have locking mechanisms 582 and 588 which may tend to secure support member 502 to support engagements 572 and 578. In some embodiments, locking mechanisms 584 and 586 may frictionally engage support member 502 when support member 502 is engaged with support engagements 572 and 578 and in other embodiments, locking mechanisms 584 and 586 may cause frictional engagement between support engagements 572 and 578 and support member 502.

Support member 502 when engaged to support engagements 572 and 578 may be rotatable about an axis tending to allow support member 502 to be positioned to extend generally perpendicular to the torso of a patient, such that when in use, support member 502 may extend outwardly from sternum engagement 572 defining a path over the breast of the patient to sternum engagement 578.

A person of skill will understand that sternum support 570 may have additional sternum engagements 572 and 576 extending outwardly from central member 580 for securing breast immobilization apparatus 503 for substantially immobilizing a second breast. Persons of skill will understand that apparatus 500 may secure either the right breast, left breast, or both breasts of a patient, and that the desired breast to be secured may dictate how apparatus 500 is configured. For example, a person of skill will understand that sternum engagements 572 and 576 will engage breast immobilization apparatus 503 in a similar manner as sternum engagements 572 and 588 engaged breast immobilization apparatus 501.

Support members 502 and 502' may be constructed from a non-magnetic material tending to reduce interference with an MRI scanner. In some embodiments, support members 502 and 502' can be made from epoxy-glass laminate, polyetherimide, for example Ultem™ manufactured by SABIC, glass filled polyetherimide, polyphenylene sulphide, glass filled polyphenylene sulphide, Radel™ manufactured by Solvay Advanced Polymers, polyaryletheretherketone, glass filled polyaryletheretherketone, polycarbonate or glass filled polycarbonate.

Deformable membrane 550 can be connected across the inner area of support member 502 and a corresponding deformable membrane 550' can be connected across the inner area of support member 502'.

Deformable membranes 550 and 550' may be constructed of a material that is non-magnetic and acoustically permeable, which may tend to prevent interference with MRI imaging and ultrasound imaging when in use. In some embodiments, deformable membranes 550 and 550' may have a magnetic permeability that will tend not to distort the homogeneity of an MRI's magnetic field more than 1 ppm. Additionally, in some embodiments, deformable membranes 550 and 550' may have an acoustic impedance less than 4 megarayleighs and additionally may have a thickness of less than $\frac{1}{12}$ of the wavelength of a 14 MHz ultrasound transducer in water with an attenuation less than 3 dB. In some embodiments, deformable membranes 550 and 550' may additionally be substantially optically transparent.

Support members 502 and 502' may be hingedly connected by hinge mechanism 530. Hinge mechanism 530 may tend to align support members 502 and 502' when breast immobilization apparatus is transitioned from an open to a closed position, the closed position tending to be the position in which breast immobilization apparatus 501 is substantially immobilizing a breast of a patient. Persons of skill will understand that other alignment mechanisms may be used.

When in use, support structures 502 and 502' may be connected together around a tissue, such as a breast, deformable membranes 550 and 550' forming a pocket to receive the breast, the pocket being formed as support structures 502 and 502' are moved into a closed position around the breast. In the closed position, deformable membranes 550 and 550' tend to press against a patient's breast so as to substantially immobilize the breast and maintain a substantially fixed geometric shape of the breast, and also to substantially maintain the position of the breast relative to the patient's torso.

Additionally, deformable membranes 550 and 550', when in use, may tend to substantially maintain breast tissue away from the torso of a patient. As such, support member 502 when engaged with corresponding support member 502' may tend to provide support tending to allow a patient to be repositioned, such as from a prone position to a supine position, and/or to stand up and move around an imaging facility between imaging sessions while maintaining a substantially fixed geometric relationship between the patient's breast and the patient's torso.

In some embodiments at least one, or both, of the surfaces of deformable membranes 550 and 550' may have an adhesive so as to be able to adhere to objects, such as tissue, for example, a breast, to be examined, or the other corresponding deformable membrane on the corresponding support member. As an example, an inner surface of deformable membranes 550 and 550' may be similar to sticky tape. In such embodiments, deformable membranes 550 and 550' may adhere to each other when in contact with one another which, when in use, may tend to further resist motion and distortion of the breast. Deformable membranes 550 and 550' may be stretchable, either elastically or plastically, as well as flexible, which may tend to allow deformable membranes 550 and 550' to conform to non-planar and non-prismatic areas of the breast. Deformable membrane 550' may additionally include a region of increased thickness 590, which may tend to resist stretching of deformable membrane 550' in the area of increased thickness 590. In some embodiments, when in use, the area of increased thickness 590 may tend to be located near the torso and may tend to provide additional support for apparatus 500.

In some embodiments deformable membranes 550 and 550' may be made from a film from the family of wound stabilizing adhesive-backed membranes made by 3M and/or Smith and Nephew. Additionally, deformable membranes 550 and 550' may have a biocompatible adhesive and film, which may tend to reduce skin trauma or residue when deformable membranes 550 and 550' are removed from contact with tissue. Additionally, deformable membranes 550 and 550' may be permanently deformable in two or more directions when pressed against a tissue, such as a breast.

In some embodiments, deformable membranes 550 and 550' may be connected to a separate membrane structure and in such embodiments may be connectable to its respective support structure 502 or 502'. In such embodiments, support structures 502 and 502' may be connectable to a respective membrane support structure such that the deformable membrane 550 and 550' may substantially cover the respective inner areas defined by support structures 502 and 502'. The membrane support structure may be a disposable portion of apparatus 500 where, when in use, a sterile membrane support structure may be used and disposed of after imaging sessions and/or interventional procedures are completed and the respective support member 502 or 502' may be a reusable portion of apparatus 500.

Figure 9:
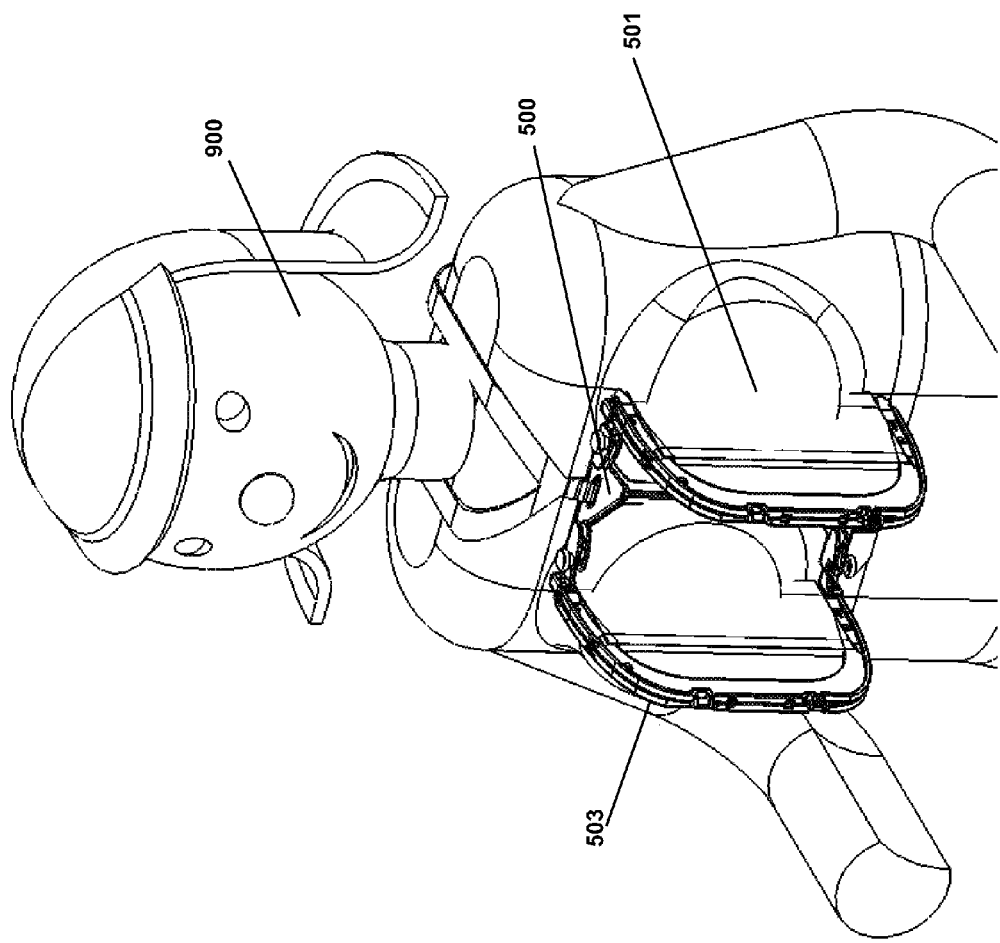
FIG. 9 shows an isometric view of the apparatus of FIG. 5 shown substantially immobilizing the breasts of a patient.

When breast immobilization apparatus 501 and 503 are each connected around the breast of a patient, as describe above, apparatus 500 shown in FIG. 9, breast immobilization apparatus 501 and 503 each tend to immobilize and/or stabilize a breast relative to the torso of patient 900.

Persons of skill will understand that breast immobilization apparatus 503 may substantially immobilize the other breast of a patient and may be comprised of substantially similar elements operating in a substantially similar manner as that of breast immobilization apparatus 501.

Figure 8:
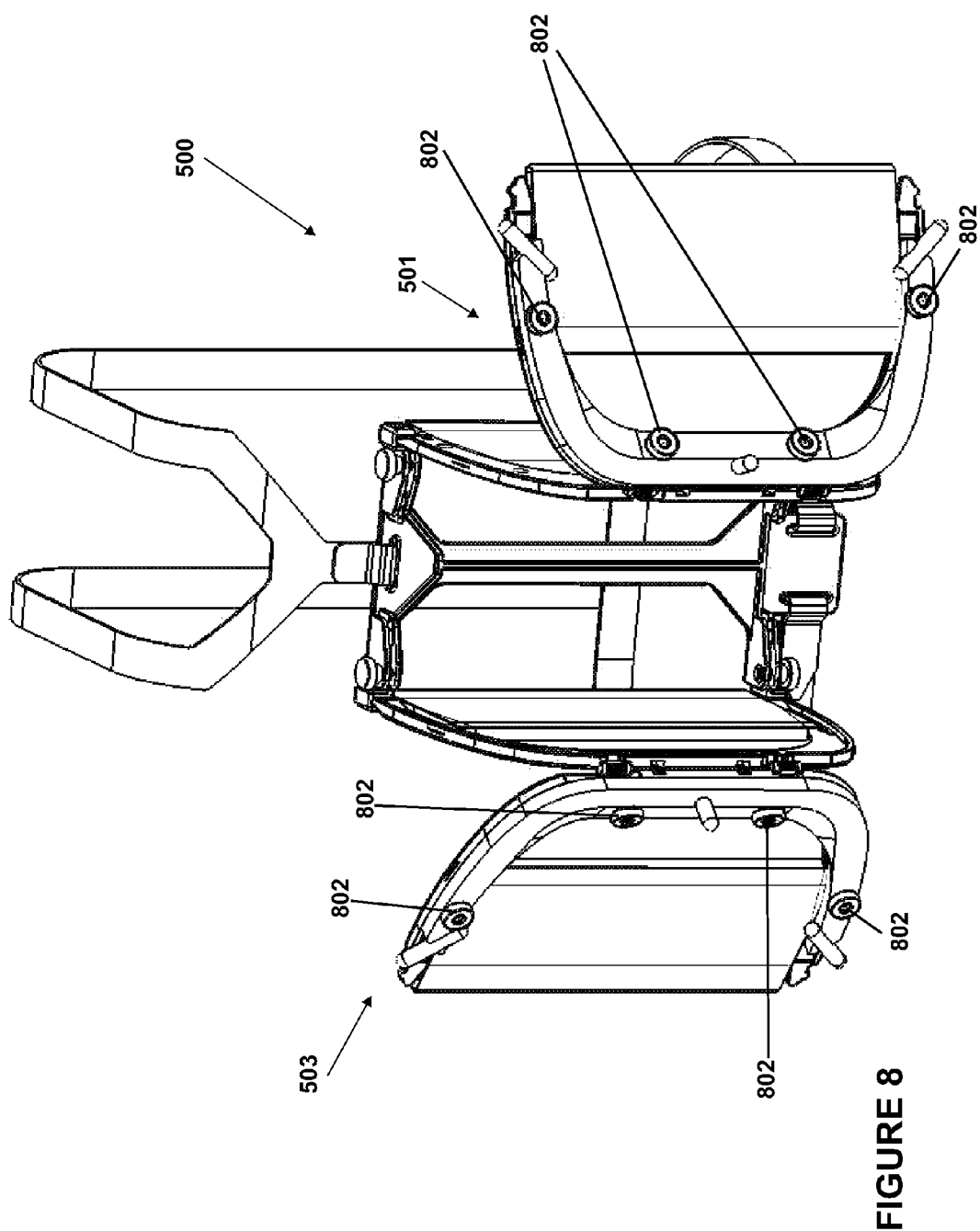
FIG. 8 shows an isometric view of an alternative embodiment of an apparatus for substantially immobilizing a breast of a patient having fiducial markers.

With reference to FIG. 8, in some embodiments, position markers, such as fiducial markers 802, may be affixed to breast immobilization apparatus 501 and 503. Fiducial markers 802 may tend to allow for images acquired with an initial imaging system, such as an MRI system, to be registered to images acquired from a subsequent imaging system, such as an ultrasound imaging system, via the known geometric relationship between the position markers, apparatus 500 and the tissue being imaged. In such embodiments, position markers, such as fiducial markers, may be visible to imaging systems and/or tracking systems, which may monitor the location and orientation of imaging equipment, such as, for example, a handheld ultrasound probe. It will be understood by those of skill in the art that position markers may be connected to any convenient element of apparatus 500.

In some embodiments, position markers may be a retroreflective dot, sphere or hemisphere, a resonant coil, an active laser, an LED light source, a radio transmitter, a radioactive pellet, an MRI fiducial, such as PinPoint™ or MR-SPOTS™ Multi-Modality Fiducial Markers by Beekley Corporation, and/or any fluid filled vessel containing between 0.5 mL and 10 mL of fluid having T1 and T2 characteristics which may tend to provide visibility on clinical MRI images. In other embodiments RF magnetic tracking may be employed, and appropriate RF sensors can be connected to any suitable location on apparatus 500.

Figure 10A:
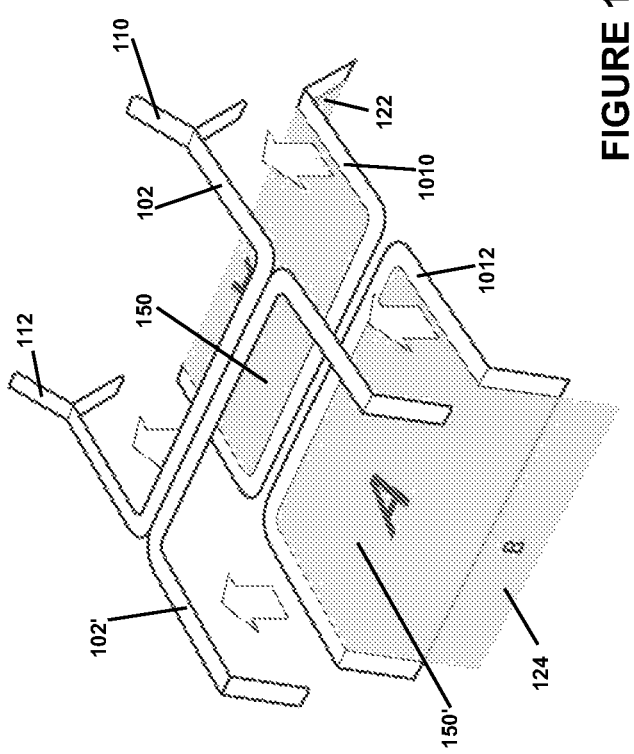

With reference to FIGS. 10A-10J apparatus 100 may be used to substantially immobilize breast 1004 of a patient 1002. With reference to FIG. 10A, membrane support 1010 may be connected to support member 102 and membrane support 1012 may be connected to support member 102'. Membrane support 1010 may define an open area which is at least partially covered by deformable membrane 150 and upon connection to support member 102, the open area defined by membrane support 1010 may be substantially aligned with inner area 104 defined by support member 102. Persons of skill will understand that membrane support 1012 may connect to support member 102' in a substantially similar manner. Membrane support members 1010 and 1012 may be connected to corresponding support members 102 and 102' by connection members, such as clips, or, in some embodiments, may be connected by an adhesive surface on deformable membranes 150 and 150' in contact with support members 102 and 102' on connection. Persons of skill will appreciate other means of connecting membrane supports 1010 and 1012 with support members 102 and 102' such that membrane supports 1010 and 1012 can maintain their position relative to support members 102 and 102'.

Bases 110 and 112 may be placed in position between a patients breast on the sternum of the patient, such that support member 102 may be aligned with the superior-inferior axis of patient 1002, as shown in FIG. 10B. Bases 110 and 112 may then be slid along the torso of patient 1002 such that support member 102 may be substantially aligned with the mid-clavicular line of patient 1002, breast 1004 tending to lie against deformable membrane 150, as shown in FIG. 10C. Additionally, in some embodiments, breast 1004 may engage with an adhesive surface of deformable membrane 150 which may tend to assist in maintaining the positioning of support member 102 during application, as shown in FIG. 10D.

Figure 10E:
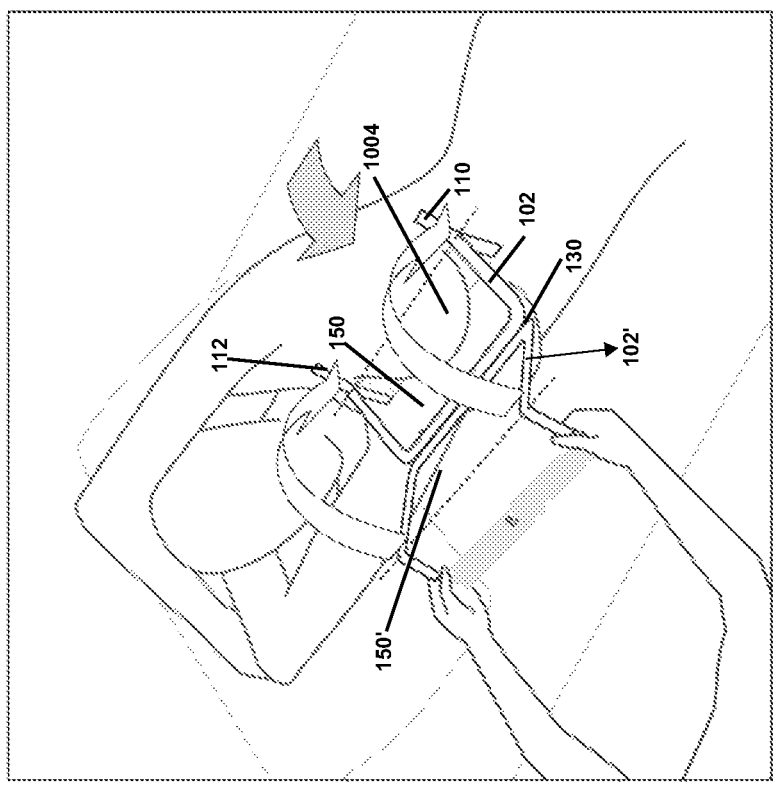

Corresponding support member 102' may be rotated about hinged connection 130, as shown in FIG. 10E, tending to position apparatus 100 into the closed position for substantially immobilizing breast 1004. As support member 102' is rotated about hinge 130, deformable membranes 150 and 150' form a pocket to receive breast 1004. With further reference to FIG. 10F, upon support member 102' rotating to the closed position, support members 102 and 102' may be locked together, tending to substantially prevent unwanted movement between support members 102 and 102'. Additionally, an adhesive surface on deformable membrane 150' may engage breast 1004.

Deformable membranes 150 and 150' may be pressed against one another and against breast 1004, deformable membranes 150 and 150' tending to press against a patient's breast so as to immobilize the breast and maintain a substantially fixed geometric shape of the breast, and also to substantially maintain the position of the breast relative to the patient's torso and, in some embodiments, tending to substantially maintain breast tissue away from the torso of a patient, as shown in FIG. 10G. Snaps 1008 may be applied to deformable membranes 150 and 150' tending to eliminate air bubbles that may be present between deformable membranes 150 and 150'.

Support feet members 118 and 120 may be positioned such that they substantially conform to the torso of patient 1002, as shown in FIG. 10H. In some embodiments, support feet members 118 and 120 may be rotated about a pin joint to substantially conform to the torso of patient 1002 tending to provide additional support to apparatus 100.

Referring to FIGS. 10I and 10J, backing 1006 may be removed from extended membrane portion 122 and may then be engaged with the torso of patient 1002, tending to provide additional support for apparatus 100.

After a breast is immobilized by way of apparatus 100, images of the breast may be scanned using, for example, an MRI scanner. After the initial imaging of the breast, the image data may be stored, for example on a computer hard-drive in a PACS format such that it may be displayed on a computer display device using standard PACS software.

Steps may be taken during the initial MRI imaging of the breast that may tend to allow for co-registration of a subsequent image. In some embodiments fiducial markers may be positioned near the tissue to be imaged. Fiducial markers may be detected by the MRI imaging system and may provide a reference marker to be referenced in any subsequent imaging session. For ultrasound imaging, the location of fiducial marker relative to the ultrasound transducer may be determined using an optical tracking system or a radio-frequency magnetic tracking system. Additional position markers or radiofrequency magnetic markers may be fixed to the ultrasound probe, allowing the known coordinates of fiducial markers in the previously acquired MRI image to be related to the current position of fiducial markers as well as the current position and orientation of the ultrasound probe. Thus fiducial markers may allow the subsequent imaging, including MRI and ultrasound, to be co-registered with the initial image data. In other embodiments, anatomic landmark references on or in the breast detected in an initial imaging session may provide a reference marker to be referenced in any subsequent imaging session.

In some embodiments, prior to performing an ultrasound imaging scan on the breast that has been immobilized within apparatus 100, ultrasound gel may be applied to the exterior surface of deformable membranes 150 and 150', without the insertion of ultrasound gel between deformable membranes 150 and 150' and the breast. Ultrasound imaging may be performed directly through deformable membranes 150 and 150'. In use, it may be desirable to perform an ultrasound imaging scan after performing an MRI imaging scan. For such uses, ultrasound gel may be applied after an MRI imaging scan has been performed, but before performing an ultrasound imaging scan. This may tend to allow the true contour of the breast to be more accurately imaged in an initial imaging session, as the MRI signal from ultrasound gel may obscure the breast contour within an image.

After any imaging procedure, an operator may perform an intervention, such as, for example, a biopsy, in some embodiments an image-guided biopsy, by inserting an interventional device, such as a biopsy needle, into the breast. In the process, the interventional device, such as a biopsy needle, may penetrate deformable membranes 150 and 150'. Additionally or alternatively, skin incisions may be made by cutting through deformable membranes 150 and 150'. In some embodiments a mechanical needle guide can be connected to one of support structure 102 and 102'. The needle guide structure tending to constrain a biopsy needle for insertion along a known axis relative to the support structure. The needle guide may take the form of a grid with multiple possible insertion points, or a single tubular shaft with angle adjustment that constrains the needle to a known trajectory and may be tracked to provide annotations on a display device during image guided intervention tending to aid image guidance, such as ultrasound guided intervention.

The present invention has been described with regard to specific embodiments. It will be appreciated that while the above embodiments have been described with complementary support structures, a greater number of structures may be used if desired and it will be obvious to persons skilled in the art that a number of variants and modifications can be made without departing from the scope of the invention as described herein.

What is claimed is:

1. An apparatus for substantially immobilizing a breast of a patient relative to a torso of the patient, the apparatus comprising:

a first support member having a first and a second base each capable of engagement with the torso, the first support member defining a first inner area and when the each base is engaged with the torso the first support member extending outwardly from the first base in a path over the breast to the second base;

a corresponding second support member removably engageable to the first support member the second support member defining a second inner area and when engaged to the first support member the first and second inner areas in substantial alignment;

a first and a second deformable membrane, the first deformable membrane removably connected to the first support member substantially covering the first inner area and the second deformable membrane removably connected to the second support member substantially covering the second inner area, the first and second membranes defining a pocket configured to receive the breast, to substantially immobilize the breast relative to the torso of the patient.

2. The apparatus of claim 1, further comprising a locking mechanism capable of locking the second support member to the first support member, when each base is engaged with the torso.

3. The apparatus of claim 2, wherein the first and the second membranes are non-magnetic and acoustically permeable.

4. The apparatus of claim 3, wherein each of the first and second membranes has a surface being an adhesive configured for adherence to at least one of the breast and the adhesive surface of the other of the membranes.

5. The apparatus of claim 4, wherein the first and second base are flexibly configured to conform to the torso of the patient.

6. The apparatus of claim 5, wherein the second base is hingedly connected to the first support member capable of engagement with a side of the torso of the patient.

7. The apparatus of claim 5, further comprising an extended membrane portion connected to at least one of the first and the second deformable membrane, the extended membrane portion having an adhesive surface capable of removable adherence to the torso.

8. The apparatus of claim 5, further comprising fidicual markers engaged to at least one of the first and second support members.

9. The apparatus of claim 5, further comprising a chest support member connected to the first and second bases capable of engagement with the torso.

10. An apparatus for substantially immobilizing a breast of a patient relative to a torso of the patient, the apparatus comprising:

a first support member having a first and a second base each capable of engagement with the torso, the first support member defining a first inner area and when the each base is engaged with the torso the first support member extending outwardly from the first base in a path over the breast to the second base;

a corresponding second support member removably hinged to the first support member such that the first and second members are moveable between an open and closed position, the second support member defining a second inner area and when engaged to the first support member the first and second inner areas are in substantial alignment when the members are in the closed position;

a first and a second deformable membrane, the first deformable membrane removably connected to the first support member substantially covering the first inner area and the second deformable membrane removably connected to the second support member substantially covering the second inner area, the first and second membranes defining a pocket configured to receive the breast as the second member is moved from the open position to the closed position, to substantially immobilize the breast relative to the torso of the patient.

11. The apparatus of claim 10, further comprising a locking mechanism capable of locking the second support member to the first support member, when each base is engaged with the torso.

12. The apparatus of claim 11, wherein the first and the second membranes are non-magnetic and acoustically permeable.

13. The apparatus of claim 12, wherein each of the first and second membranes has a surface having an adhesive configured for adherence to at least one of the breast and the adhesive surface of the other of the membranes.

14. The apparatus of claim 13, wherein the first and second bases are flexibly configured to conform to the torso of the patient.

15. The apparatus of claim 14, wherein the second base in hingedly connected to the first support member capable of engagement with a side of the torso of the patient.

16. The apparatus of claim 14, further comprising an extended membrane portion connected to at least one of the first and the second deformable membrane, the extended membrane portion having an adhesive surface capable of removable adherence to the torso.

17. The apparatus of claim 14, further comprising fiducial markers engaged to at least one of the first and second support members.

18. The apparatus of claim 14, further comprising a chest support member connected to the first and second bases capable of engagement with the torso.

19. An apparatus for substantially immobilizing a breast of a patient relative to a torso of the patient, the apparatus comprising:
   a breast support comprising:
      a first support member defining a first inner area;
      a corresponding second support member defining a second inner area, removably hinged to the first support member, such that the first and second members are moveable between an open and closed position, the second support member defining a second inner area and when engaged to the first support member the first and second inner areas are in substantial alignment when the members are in the closed position;
      a first and a second deformable membrane, the first deformable membrane removably connected to the first support member substantially covering the first inner area and the second deformable membrane removably connected to the second support member substantially covering the second inner area, the first and second membranes defining a pocket configured to receive the breast as the second member is moved from the open position to the closed position, to substantially immobilize the breast relative to the torso of the patient;
   a harness comprising:
      a sternum support capable of engagement with the torso substantially along a sternum of the patient;
      a first and a second support engagement member extending from the sternum support towards the breast, the first support member coupled to the first and second support engagement members and extending outwardly from the first support engagement member in a path over the breast to the second support engagement member; and
      an adjustable strap connected to the sternum support capable of securing the patient to the sternum support.

20. The apparatus of claim 19, further comprising a locking mechanism capable of locking the second support member to the first support member, when each base is configured to be engaged with the torso.

21. The apparatus of claim 20, wherein the first and the second membranes are non-magnetic and acoustically permeable.

22. The apparatus of claim 21, wherein each of the first and second membranes has a surface having an adhesive configured for adherence to at least one of the breast and the adhesive surface of the other of the membranes.

23. The apparatus of claim 22, further comprising an extended membrane portion connected to the second deformable membrane, the extended membrane portion having an adhesive surface capable of removable adherence to the torso.

24. The apparatus of claim 22, further comprising fiducial markers engaged to at least one of the first and second support members.

25. The apparatus of claim 19, further comprising a corresponding second breast support coupled to the sternum support capable of substantially immobilizing a second breast of the patient.

* * * * *